(12) United States Patent
Link et al.

(10) Patent No.: US 10,675,097 B2
(45) Date of Patent: Jun. 9, 2020

(54) HANDHELD SURGICAL TOOL WITH AUTONOMOUS NAVIGATION

(71) Applicant: Waldemar Link GmbH & Co. KG, Hamburg (DE)

(72) Inventors: Helmut D. Link, Hamburg (DE); Riccardo Signoretti, Jersey City, NJ (US)

(73) Assignee: Waldemar Link GmbH & Co. KG, Hamburg (DE)

( * ) Notice: Subject to any disclaimer, the term of this patent is extended or adjusted under 35 U.S.C. 154(b) by 338 days.

(21) Appl. No.: 15/507,114

(22) PCT Filed: Aug. 28, 2015

(86) PCT No.: PCT/EP2015/069761
§ 371 (c)(1),
(2) Date: Feb. 27, 2017

(87) PCT Pub. No.: WO2016/030512
PCT Pub. Date: Mar. 3, 2016

(65) Prior Publication Data
US 2017/0252110 A1 Sep. 7, 2017

(30) Foreign Application Priority Data
Aug. 28, 2014 (EP) .................................... 14182589

(51) Int. Cl.
*A61B 34/20* (2016.01)
*A61B 34/00* (2016.01)
(Continued)

(52) U.S. Cl.
CPC .......... *A61B 34/20* (2016.02); *A61B 17/7074* (2013.01); *A61B 34/76* (2016.02);
(Continued)

(58) Field of Classification Search
CPC ..... A61B 34/20; A61B 34/76; A61B 17/7074; A61B 2034/2048; A61B 2090/376;
(Continued)

(56) References Cited

U.S. PATENT DOCUMENTS 8,057,482 B2 11/2011 Stone et al.
2006/0142657 A1* 6/2006 Quaid .................... G06F 19/00
600/424

(Continued)

FOREIGN PATENT DOCUMENTS

WO WO-2011/089606 7/2011

OTHER PUBLICATIONS

International Search Report and Written Opinion dated Oct. 16, 2015, directed to International Application No. PCT/EP2015/069761; 14 pages.

*Primary Examiner* — Elmer M Chao
(74) *Attorney, Agent, or Firm* — Joseph V. Saphia; Haug Partners LLP

(57) ABSTRACT

A handheld surgical tool includes a handle, an instrument shaft, and a navigation device, which includes at least one sensor unit for sensing positional data, a computing unit configured to determine a position in space based on signals of the sensor unit, at least one set key and a position memory configured to store a data set for a position upon activation of the at least one set key. A comparator is operatively connected to the position memory for comparing an actual position against a stored position in at least two different operation modes and for generation of a deviation signal, wherein operation modes differ in that a first mode is configured for a reduced comparison only which lacks at least one spatial dimension. A feedback device is provided supplied with the deviation signal and being configured to indicate direction and preferably magnitude of any deviation.

25 Claims, 5 Drawing Sheets a)

b)

c)

d)

(51) Int. Cl.
*A61B 17/70* (2006.01)
*A61B 17/00* (2006.01)
*A61B 90/00* (2016.01)

(52) U.S. Cl.
CPC .............. *A61B 2017/00119* (2013.01); *A61B 2017/00203* (2013.01); *A61B 2017/00734* (2013.01); *A61B 2034/2048* (2016.02); *A61B 2090/376* (2016.02); *A61B 2090/3764* (2016.02); *A61B 2562/0219* (2013.01); *A61B 2562/0223* (2013.01)

(58) Field of Classification Search
CPC ........... A61B 2017/00119; A61B 2017/00203; A61B 2017/00734; A61B 2562/0219; A61B 2562/0223
See application file for complete search history.

(56) References Cited

U.S. PATENT DOCUMENTS

| | | |
|---|---|---|
| 2013/0244196 A1 | 9/2013 | Goodacre |
| 2013/0253599 A1* | 9/2013 | Gorek .................... A61B 34/20 606/86 A |
| 2014/0200439 A1 | 7/2014 | Barsoum et al. |

* cited by examiner

HANDHELD SURGICAL TOOL WITH AUTONOMOUS NAVIGATION

CROSS-REFERENCE TO RELATED APPLICATION

This Application is a U.S. National Stage application under 35 USC 371 of International Application No. PCT/EP2015/069761, filed Aug. 28, 2015, which claims priority to European Application No. 14182589.3, filed Aug. 28, 2014, the entire contents of which are incorporated herein by reference.

FIELD OF INVENTION

The invention relates to a handheld surgical tool with autonomous navigation. The handheld surgical tool comprises a handle, an instrument shaft and a navigation device, the navigation device comprising a set key and a position memory configured to store a data set for a position upon activation of the set key.

BACKGROUND OF THE INVENTION

Fine scale surgery, e.g. for placing implants at a spinal column, demands a high degree of positional accuracy. However with minimally invasive surgery, direct visual control of positioning of any instruments used by the surgeon is rather difficult. Sufficient visual control can often only be achieved by use of dedicated equipment, in particular picture generating devices, e.g. C-arm providing fluoroscopic control and/or sophisticated navigation systems forming a part of the operating room. However, such sophisticated navigation systems are expensive, complex to operate and as a result sparsely available and used. C-arm devices, on the other hand, are more readily available and surgeons are accustomed to their usage. However, continued use of the C-arm device provides rather a high radiation dose. Further, most C-arms have only one direction of view and consequently require intraoperative repositioning quite often, which can be detrimental to positional accuracy and is time consuming.

In order to provide a device which is easier to use and still provides an improved positional accuracy a handheld surgical tool was developed which features an autonomous navigation device (U.S. Pat. No. 8,057,482 B2). The tool features a button which has to be pressed when the device achieves its basic reference position. Thereby all positional data are set to zero. Once this is accomplished, the tool can be freely manipulated by the surgeon, and it will show its positioning in space on three numerical displays provided at its casing. The displays show three-dimensional angular orientation of the tool in space. This device is in an improvement in terms of determine positioning of the tool in an area with limited access and consequently restricted visual observance. However, it can be rather difficult for the surgeon to control the plurality of displays in order to check whether a desired orientation has already been reached or is maintained.

SUMMARY OF THE INVENTION

It is an object of the invention to provide an improved handheld surgical tool which is easier to handle. A solution according to one aspect of the invention results in the features of the independent claim; preferred embodiments are the subject of the dependent claims. The invention further relates to a corresponding method.

According to an aspect of the present invention, a handheld surgical tool with autonomous navigation, comprising a handle, an instrument shaft and a navigation device, the navigation device comprising at least one sensor unit for sensing positional data, a computing unit configured to determine a position in space based on signals of the sensor unit, at least one set key and a position memory configured to store a data set for an actual position upon activation of the at least one set key, is provided with a comparator operatively connected to the position memory, the comparator being configured for comparing an actual position against a position stored in the position memory in at least two different operation modes and for generation of a deviation signal, wherein a first operation differs from the second operation mode in that it is configured for a reduced comparison only which lacks at least one spatial dimension opposed to the second operation mode, and a feedback device is provided supplied with the first and/or second deviation signal and being configured to indicate direction, and preferably magnitude, of any deviation.

The term "position in space" and its short form "position" in context of the present invention generally refers to a system with six degrees of freedom that may comprise absolute location and orientation. The location might be represented as coordinates of a three-dimensional space with perpendicular axes (e.g. X, Y, Z), while the orientation might be provided as Euler angles, especially as yaw, pitch and roll. It may be preferred in the present invention if the "position" in a simplified version refers only to the orientation of the tool, more preferably only to the yaw and pitch of the tool.

The "instrument shaft" may be an actual instrument itself. However, it may also be configured as an attachment point enabled to receive an instrument in an interchangeable fashion.

Aspects of the invention provide a comparator having two distinct operating modes in combination with position memory, wherein in one of the two distinct operating modes only a reduced position indication is processed. The reduced position indication is a position indication which lacks at least one indication for one degree of freedom compared to the full position indication of the second operating mode. E.g. if the absolute location does not need to be monitored, in Euclidean space three angle indications can be used to describe an orientation of a device in a three-dimensional space. Using only two instead of three of such angles will not provide a fully fixed orientation, but will instead retain one degree of freedom. If e.g. angles for roll, pitch and yaw are used, than an incomplete position indication could only have indications for e.g. roll and yaw, leaving pitch as a degree of freedom; if only two rather than three angles are to be used (e.g. if roll is to be ignored) a full position indication will have pitch and yaw, whereas an incomplete position indication may indicate yaw only.

In its first operation mode the comparator is configured to compare an actual position determined from the navigation device against an incomplete position indication stored in the position memory. The comparator detects whether a present position of the tool is in conformity with the stored incomplete position indication, and if it is not it will provide a deviation signal. In the above mentioned simplified example using just two angles, the incomplete position data only comprises yaw. By pressing of a set key the position will be stored in the position memory as an incomplete position indication. The comparator will then detect any deviation from the stored value for yaw, while pitch is still freely modifiable. The user may reposition the tool such that its actual yaw angles matches the stored one. By virtue of this, yaw angle of the tool can be locked in.

Preferably, in this first operation mode the indication of said at least one spatial dimension is suppressed. In the present example this means that no pitch angle information will be displayed (since this is the spatial dimension by which the first operation mode is reduced), thereby leaving a yaw angle only indication. Surprisingly, by reducing the amount of information displayed, namely by suppressing indication of the spatial dimension by which the first operation mode is reduced, the display presented to the operator is simplified. It thereby provides a better concentration on the relevant aspect. In other words, the reduction of the display by said at least one spatial dimension prides a benefit to the operator in maintaining proper positioning.

Upon user command, by a further actuation of the set key used before or of a second set key the comparator will be switched from the first to the second operation mode. In its second operation mode the comparator utilizes the full position indication. In the above example, this will bring the pitch angle additionally into consideration. In this operating mode, the comparator checks yaw angle as well as pitch angle against the value stored in the position memory, thereby locking in yaw angle as well as pitch angle. In this case, the feedback device shows indications in all those angles monitored by the comparator (as supposed to the first operation mode, wherein indication of pitch angle was suppressed and only yaw angle was indicated).

By virtue of this, the surgeon can precisely acquire a position corresponding to a given track by orienting the surgical tool in a two-step fashion. In the first step according to the example, the surgeon needs to concentrate on positioning of the tool in one plane only, and sets this position by pressing the set key. Then the comparator in its first operating mode will track and show any deviation. The surgeon may then concentrate on positioning the tool to a desired pitch angle, and while doing so he is of no risk of losing the yaw position as the comparator is having a watch thereon. If the desired position in the other plane (in the example: pitch) is achieved, too, then the full position will be locked-in by a further actuation of the set key used before or of a second set key. In essence, the surgeon needs to concentrate on achieving one orientation at a time only, as the comparator has a watch on one (first operation mode) or two (second operation mode). At no time is the surgeon at risk of losing a position once achieved, since the tool itself keeps track of any deviation and thus allows the surgeon to regain the set position.

In an example the surgeon might position the tool in a first plane that might be defined by a picture generating device. For example, the first plane might be the anterior-posterior plane, where a picture is generated by a correspondingly orientated C-arm. With the help of the generated picture, the surgeon might define the desired starting point and the desired trajectory of the tool in this plane using known anatomic landmarks visible on the generated picture and places the inventive tool accordingly. The surgeon can then freeze the trajectory in the anterior-posterior plane by pressing a set key on the inventive tool. Afterwards the C-arm is rotated so that the picture generated shows e.g. the lateral plane. The surgeon might then define the desired trajectory of the tool in this plane. While doing this, the inventive tool helps the surgeon to keep the correct orientation in the anterior-posterior plane defined before. Once he has found the correct trajectory in the lateral plane, he might freeze this as well by pressing a set key on the inventive tool. After this, the desired trajectory is fully defined and the inventive tool supports the surgeon to maintain its correct orientation without requiring any further picture generation.

It is much easier to manipulate the instrument that way as to control all axis at once, as it was necessary with the handheld instrument according to the state of the art which lacks any locking-in as the inventive tool does. As a result, the surgical tool according to the present invention is much easier to handle.

In a preferred embodiment the feedback devices can be configured such as to show the deviation qualitatively, preferably non-numerically. The feedback device can further be configured for visual, aural and/or tactile indication. Providing a non-numerical indication alleviates the surgeon from the task of interpreting a numerical reading comparing it against any target number which requires considerable mental capacity. This is even truer if three numerical indications have to be kept under control at once, as it was necessary with the handheld tool of the prior. Providing a non-numerical indication gives an easy cue to the surgeon whenever deviations occur, without requiring him to perform mental calculations. An example for such non-numerical deviation indication could be a set of dots arranged in a crosshair manner, wherein one dot is highlighted in each bar of the crosshair to show current deviation. An example for an aural indication is a variably pitched tone for an indication in one direction; further, tone pauses can be used, like providing a continuous tone in the correct position and a dash like tone sequence for deviations to one side and a dot like sequence for a deviation to the other side, merging into a continuous tone upon reaching the correct position. Example for a tactile indication are vibrating elements placing on each side of the handle, thereby signaling the operating surgeon in a very intuitive manner to which direction a deviation occurs; the vibrating will stop upon reaching the correct position.

Preferably, the feedback device comprises a tolerance module which is configured to suppress indicating of a deviation signal a presetable threshold. The tolerance module maybe configured as a deadband providing a certain tolerance around the correct position. Thereby, an over sensitive operation of the feedback device could be avoided. As an example, the tolerance module may accept deviation of up to two degrees, and it will start signaly deviation once it becomes greater than two degrees.

Preferably a remote display for indication is provided. While the tool itself may give a direct sensing to the user by means of its feedback device, a remote display provides the information to other persons, too.

Further preferably, a two-part configuration of the feedback device such that a remote display will be the only display of the feedback device. Thereby no display is necessary on the tool itself, which is beneficial e.g. for space considerations in the case of small tools or for reasons of easier sterilization.

Further, the remote display may comprise a hybrid display with other, e.g. fluoroscopic imagery of the patient, so that the positional relation of the surgical tool to the patient can be seen directly on the remote display.

In a further preferred embodiment, an interface may be provided that is configured to supply positional data of the handheld surgical tool to an external system, e.g. an operating theatre navigation system. The interface may also be configured to drive a remote display for the feedback device, preferably using Bluetooth, WiFi or MirrorLink technology.

Preferably, a reference base is provided at an exterior surface of the tool, and further preferably a key is provided configured to zero the navigation unit. Thereby the surgical tool can be synchronized with a static frame acting as a reference in respect to the surroundings, namely the operation theatre including the operating table on which the patient is located. By providing a reference base on the exterior surface a calibration by the zeroing can be achieved most easily by just placing the surgical tool on set reference base on a horizontal plane, like the operation table, and pressing the key for zeroing.

Preferably, an offset device is provided which is configured to determine the position of a tip of the instrument shaft and/or another instrument attached to the instrument shaft. The offset device interacts with the navigation device in such a manner as to compute the position of a tip of the instrument shaft based on the navigation data collected for the positioning of the surgical tool. Thereby it is enabled to determine whether the tip of the instrument has already reached a desired position. This is of particular relevance if the handheld surgical tool is to be coupled with other image creating device in order to give a proper visualization of the position of the tip in respect to the patient's body. If different instruments are to be attached, the offset device must be programmed accordingly in order to compensate for different lengths or angular orientation of various instruments.

Preferably, the position memory to which the comparator is operatively connected is a duplex memory having a first and second memory unit. The second memory unit is configured for storing a full data set for the position forming a full position indication, whereas the first memory unit is configured for storing of a subset only. The subset lacks data for at least one degree of freedom in the position in space to form an incomplete position indication. By providing two memory units the comparator can selectively access them depending on its operation mode. In its first operation mode it is configured to recall the stored incomplete position indication, to compare it against an actual position indication and to generate a first deviation signal for one spatial direction; and in its second operation mode the comparator is configured to recall the full position indication, to compare it against the actual position indication and to generate a second deviation signal which is two-dimensional.

Preferably, the handheld surgical tool is configured with a rechargeable battery and a wireless charging unit. Thereby no external contacts would be required for powering of the surgical tool, thereby facilitating cleaning of the surgical tool after use.

Preferable, the set keys of the surgical tool can be configured as a momentary switch, a sensor switch or a voice controlled switch. A conventional momentary switch acting mechanically is the simplest embodiment. A sensor switch is advantageous in that it does not need to have moveable contact and can be cleaned easily. A voice control switch is convenient to use, as the surgeon does not have to press a switch or place his finger on a sensor surface. Instead it will suffice to speak out loudly a certain phrase, like "Freeze" in order to achieve a desired action.

In preferred embodiment the sensor unit is selected from a group comprising accelerometers, rate gyroscopes and magnetometers, all preferably having at least a 3-axis configuration.

Preferably, the handheld surgical tool and/or the navigation device comprises a status indicator, e.g. a status LED. The status indicator might indicate whether the navigation device is switched on, whether the battery level is low and/or in case there is communication with e.g. a feedback device or another external system.

The invention further relates to a method for orienting, in particular outside the human body, a handheld surgical tool with autonomous navigation, the handheld surgical tool comprising a handle, an instrument shaft and a navigation device, the navigation device comprising at least one sensor unit for sensing positional data, a computing unit configured to determine a position in space based on signals of the sensor unit, at least one set key and a position memory configured to store a data set for a position upon activation of the at least one set key, and a comparator operatively connected to the position memory, further comprising providing positional data with a full position indication and a subset being reduced by one spatial dimension, comparing an actual position against a position stored in the position memory using the subset being reduced by one spatial dimension in a first operation mode, generating a first deviation signal based on a result of the comparing, switching to a second operation mode by command, comparing an actual position against a position stored in the position memory using full positional data, providing a feedback about direction and preferably magnitude of any deviation to the user in the first operation mode and in the second operation mode. For further details reference is made to the explanations given above.

BRIEF DESCRIPTION OF THE DRAWINGS

The invention will further be described in more detail with the regard to accompanying drawing. The figures of the drawing show.

DETAILED DESCRIPTION OF THE INVENTION

Figure 1:
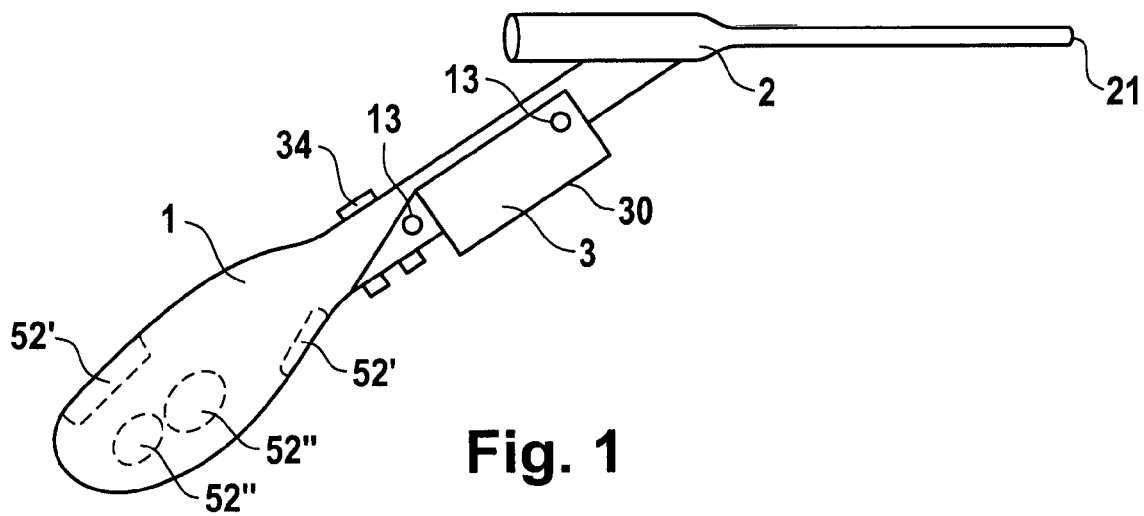
FIG. 1: a side view of a preferred embodiment of the invention.

A preferred embodiment for a handheld surgical tool according to the present invention is shown in FIG. 1. The surgical tool comprises as main components a handle 1, an instrument shaft 2 and a navigation device 3. The instrument shaft 2 in this depicted embodiment is a wire guide having an internal hollow conduit for guiding a surgical wire to be placed at a bone. In order to place the surgical wire in a correct manner, the wire guide must be placed with its tip on the target location in a certain orientation which determine the angle with which the wire will enter the bone material. The wire guide may be exchanged against other instruments if desired.

The navigation device 3 is in the depicted embodiment releasably connected to the handle 1 by means of connecting splints 13. It is to be noted that such a detachable configuration is an option and the navigation device 3 may well be integrated into the handle 1, alternatively.

Figure 2:
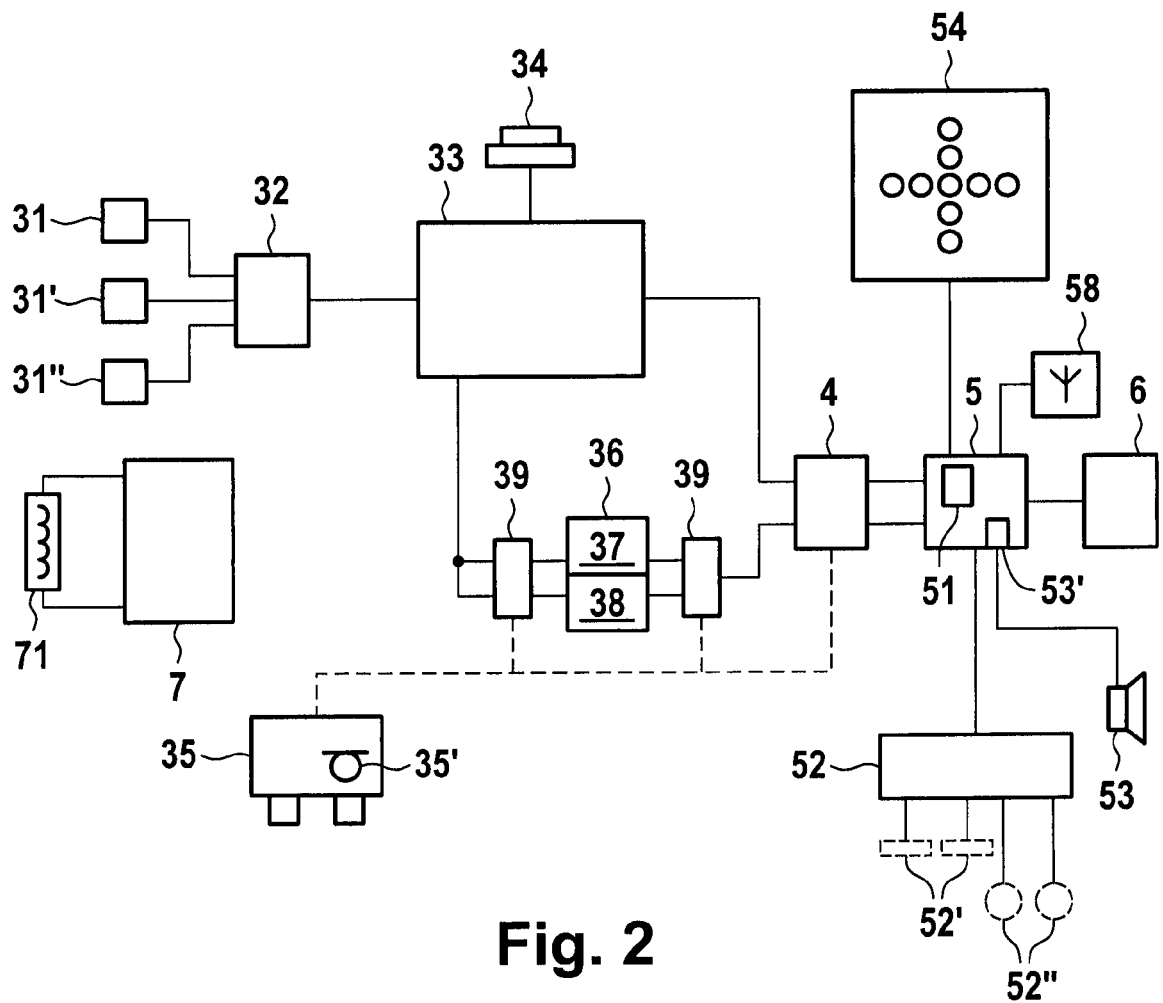
FIG. 2: a schematic view showing function blocks of the preferred embodiment of FIG. 1.
Figure 3:
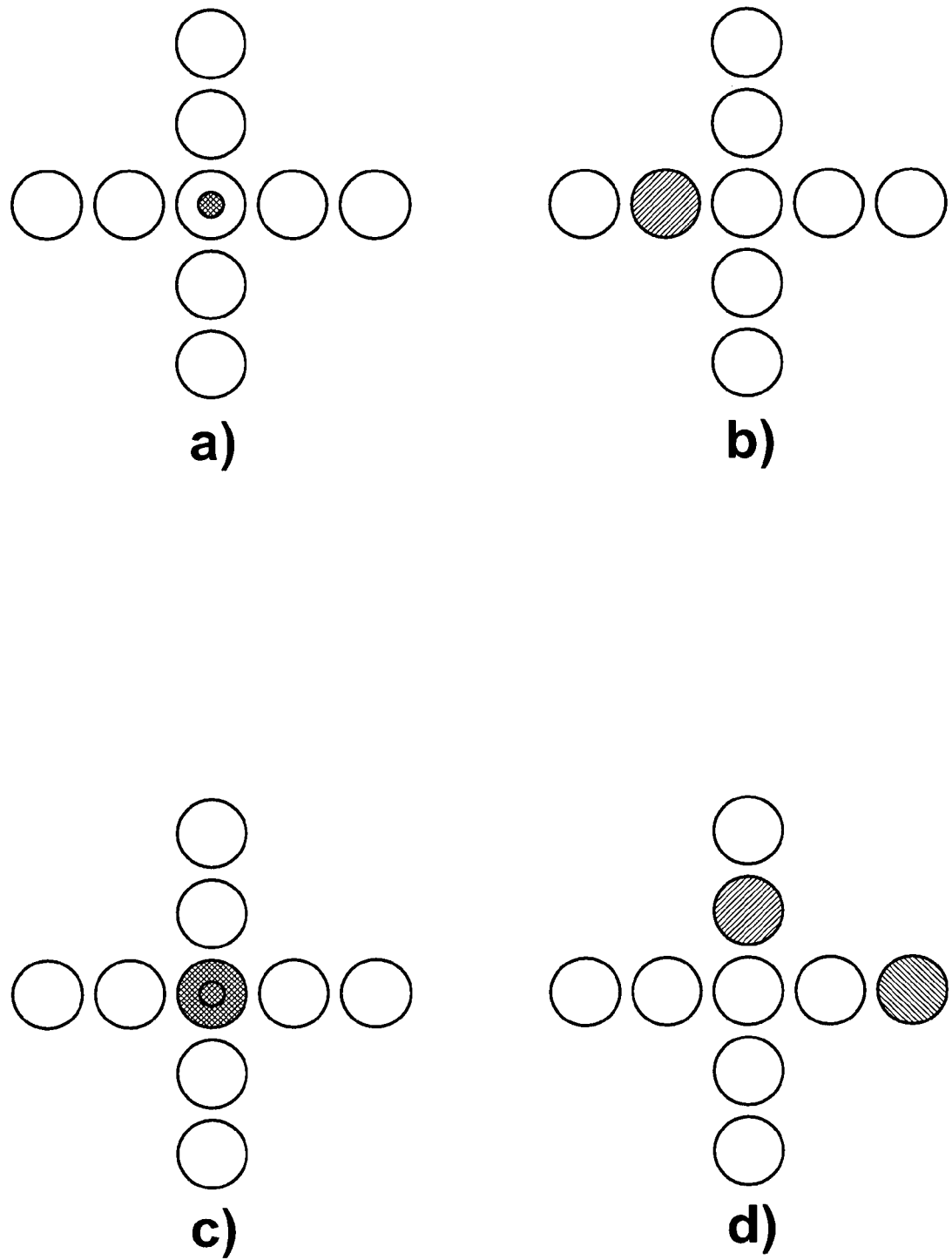
FIG. 3: an example for a feedback device using a visual indication.

A functional explanation of the handheld surgical tool according to the preferred embodiment will be given with reference to FIGS. 2 and 3. The navigation device 3 comprises at least one (in the depicted embodiment three different) sets of sensor units 31, 31', 31", the sensor units being a 3-axis accelerometer, 3-axis rate gyroscopes and a 3-axis magnetometer, respectively. Each sensor unit 31, 31', 31" on its own produces positional information independently from each other, said positional information comprising e.g. acceleration or other positional data from yaw, roll and pitch reference to the body frame of the handheld surgical tool. The three sensor units 31, 31', 31" are connected to a data fusion module 32. It is configured to process the output signals of the sensor units in a generally known manner (filtering, normalizing, calibrating etc.) and further to merge the processed signals in order to produce a unified consolidated position output signal. For this merging generally known techniques are used (like Kalman-filter, Quaternion-gradient, or complementary filter etc.). Optionally, the data fusion module 32 is further configured to code the output by Quaternions in order to avoid gimbal lock issues.

The consolidated output position signal of the data fusion module 32 is applied to the computing unit 33. Based on this signal a conversion to Euler angles is performed by successive projection on the planes of a 3D-Euclidean space, thereby forming a trajectory definition. The trajectory definition which is defined by e.g. angles for yaw and pitch can be stored in a position memory 36.

The position memory 36 comprises a first memory unit 37 and a second memory unit 38. The second memory unit 38 is configured for storing a full data set for the position as determined by the computing unit 33. In contrast, the first memory unit 37 is configured for storing of a subset of the position data set only, wherein the subset lacks data for at least one degree of freedom regarding the spatial position of the instrument. In the preferred embodiment, that degree of freedom for which data is lacking may be the pitch angle. Storing and recalling of data into and from the first and second memory unit 37, 38 is controlled by the selector 39 which is operatively connected to set key 35 which is further connected to a comparator 4.

As an alternative to the set key 35, a microphone 35' may be provided. Thereby, a voice activation could be substituted for physical pressing of the set key 35. Speaking a command word like "freeze" may thus substitute pressing of the set key in order to lock in heading/pitch as desired.

The comparator 4 is operatively connected to the position memory 36, the computing unit 33 and to the set key 35. Further, it is configured to recall data from the first memory unit 37 or the second memory unit 38 depending on an operation mode. The operator 4 is configured for two operation notes. The operation mode may be selected by the set key 35. In a first operation mode, the comparator 4 is configured to recall the stored incomplete position from the first memory unit 37 and to compare it against an actual position indication as supplied by the navigation computing unit 33. Based on the difference between these position indications, the comparator 4 generates a first deviation signal for one special direction, namely yaw in the preferred embodiment. In the second operation mode, the comparator 4 is configured to recall the full position indication from the second memory unit 38 and to compare it against the actual position indication as supplied by the computing unit 33. Based on the difference between these position indications it generates a second deviation signal which has one more dimension than the first deviation signal, namely yaw and pitch in the preferred embodiment. Switching from the first to the second operation mode is controlled by the user by means of set key 35.

Further, a feedback device 5 is provided to which the first and second deviation signal is supplied. The feedback device 5 is configured to indicate direction—and in a qualitative manner magnitude of any deviation as defined by the first or second deviation signal. In the preferred embodiment, the feedback device is configured for a tactile indicator 52, an aural indicator 53. Further, as part of a two-piece construction a visual indicator is provided, the visual indicator being formed by a display 54 of a separate device. The display 54 forming the visual indicator comprises two orthogonal growths of lighted dots arranged in a crosshair pattern (see FIG. 3). The tactile indicator 52 comprises two pairs of vibration transducers 52' and 52" arranged on opposite lateral sides of the handle 1 and on the top and bottom side of the handle 1, respectively. As an aural indicator a loudspeaker 53 is provided which is driven by a sound module 53' forming a part of the feedback device 5. Further, the feedback device 5 is configured with a wireless transmitter 58 configured for communication with a remote display, which can be a tablet computer, and/or other navigation systems present in the operation theatre.

Further, an offset device 6 is provided. It is configured to determine the position of a tip of the instrument 2 attached to the handle 1. Data regarding a distance between a tip 21 and the sensors 31, 31', 31" of the navigation device 3 and the angle at which the instrument 2 is orientated against the handle 1 is preset in the offset device 6. Thereby the offset device 6 is enabled to modify position indications of the navigation unit 33 such that it is the position of the tip 21 which is the base for triggering the feedback device 5 rather than a position of the navigation device 3 proper. The offset device 6 needs to be adjusted if a different instrument 2 having a different length or being angled differently is to be attached. To this effect setting means (not shown) are provided.

Yet further, a rechargeable battery 7 is provided which supplies the various components of the handheld surgical tool. The supply lines are not shown FIG. 2. In order to recharge the battery 7 a recharging coil 71 is provided which is configured for wireless charging.

Operation of the handheld surgical tool and its indications as effected by the feedback device 5 will be described in the following.

As a first step, the user will place the instrument on a flat surface, preferably the operation table. The instrument shall be placed with the reference base 30 at the bottom of the navigation device 3 flat on the table. This defines a zero position and is acknowledged by pressing of a zero set knob 34. This sets a body frame of the instrument which a reference frame of the operating room.

Figure 4B:
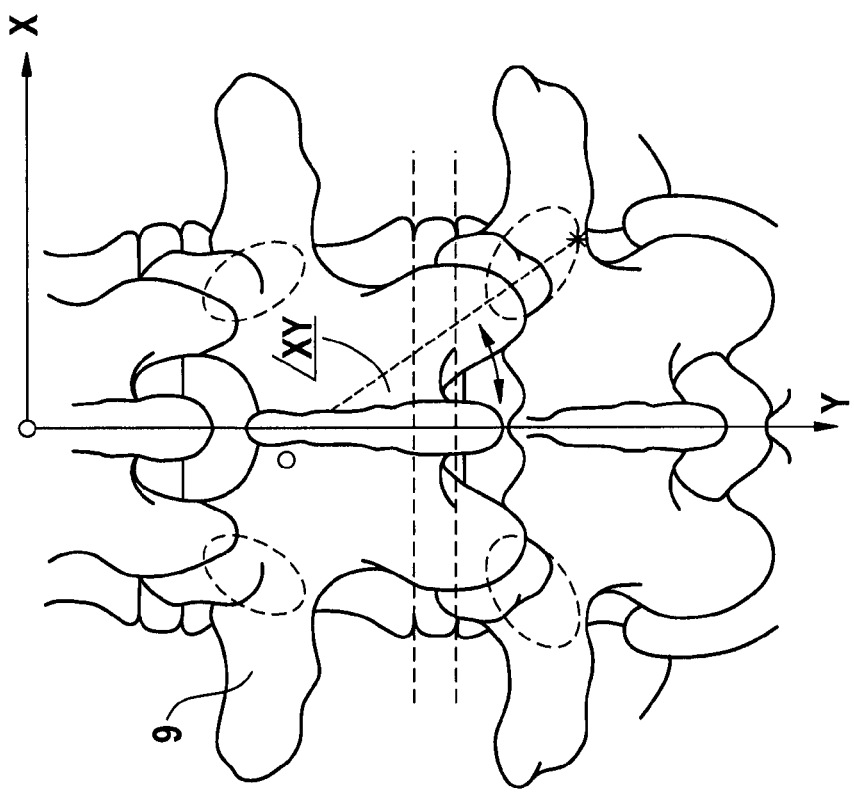
FIG. 4a, b: an overview of a C-arm placed at an operational table in a first orientation and a detailed view of a part of the spinal column of a patient.

In a second step, the user will take the instrument and place it at a desired position. Positioning will be performed under fluoroscopic control as effected by a C-arm 88. For the sake of discussion it shall be assumed that the C-arm is oriented vertically, such as to provide a view along an A/P direction of a patient placed on the operating table 89 (see FIG. 4). The fluoroscopic view may be presented to the surgery team by means of a conventional observation screen device 8 (see FIG. 5). The fluoroscopic view achieved in the situation is shown in FIG. 4b.

Figure 4A:
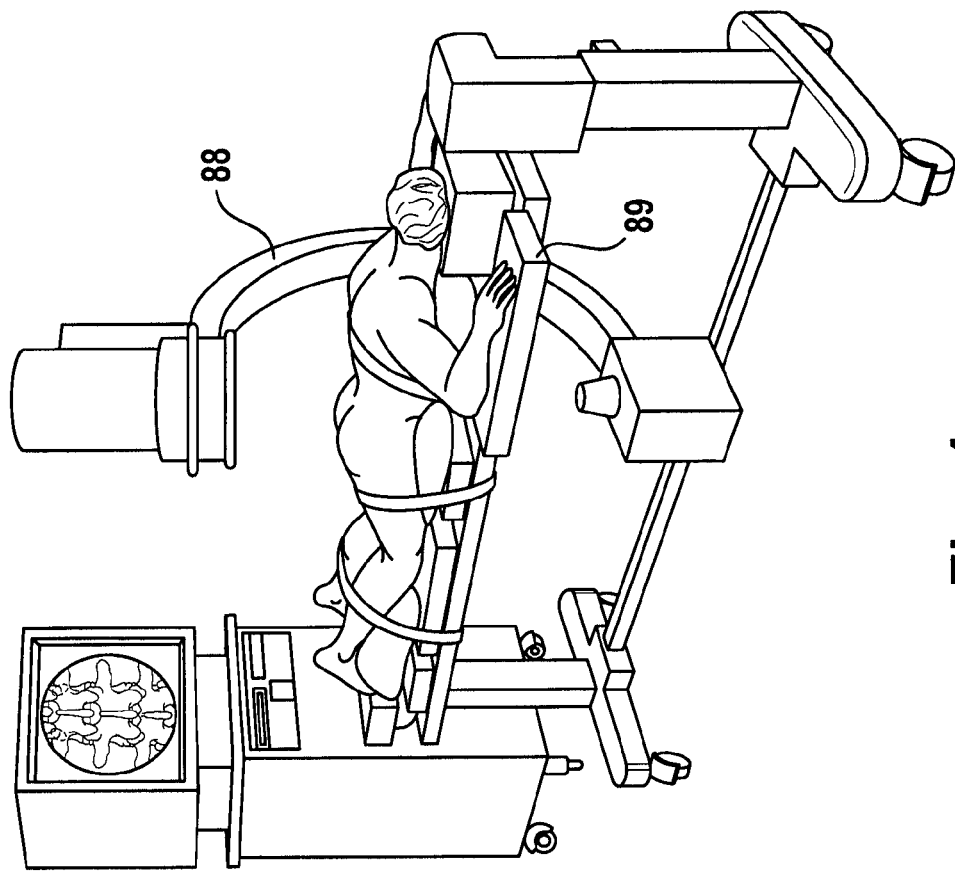

By means of definition, a coordinate system for the human body shall be defined featuring an X-axis as side to side, a Y-axis as up and down, and a Z-axis orthogonal to the X- and Y-axis indicating depth. Thereby, an anterior-posterior view as achieved in FIG. 4 provides information regarding a trajectory relative to the X/Y-plane. In this view, the cephalo-caudal and medial-lateral orientation can be appreciated, as the surgeon will be able to see the defined starting point (marked by a small circle at the begin of a dashed line in FIGS. 4b and 5b) of the guidewire (or stymen pin, screw, etc.) as well as the endpoint of the desired trajectory (marked by a star symbol at the end of the dashed line in FIGS. 4b and 5b). For example, for a translaminar facet screw, the desired endpoint on the AP view would be the infero-lateral cortex of the pedicle. The line between the defined starting point and the desired endpoint can be calculated as an angle or trajectory relative to the X-axis and the Y-axis. Once the targeting instrument is moved with its tip 21 to the starting point and is oriented towards the desired endpoint, the surgeon will be able to press the set key 35 (or alert the system verbally) to confirm acceptance of this trajectory as illustrated in FIG. 4b. It is to be noted that the targeting instrument itself remains outside of the human body and the orienting happens outside of the human body.

When this trajectory is accepted by the surgeon, the navigation device 3 stores the corresponding positional data set upon pressing of the set key 35 in the first memory unit 37. This sets a first angle, e.g. yaw for the preferred embodiment. As long as the handheld surgical tool is held by the surgeon with the correct yaw angle (heading), an indication will be provided by the feedback device 5 similar to that of FIG. 3a. In case that a yaw error were to occur, then the light would wander along the horizontal axis depending on the magnitude of the heading deviation. For example, FIG. 3b shows a mild (but no longer tolerable) deviation to the left. Thereby, the yaw position is locked-in, and the surgeon can find it again by reference to the visual indication and by re-centering it such as to get an indication as shown in FIG. 3a. It is to be noted that no pitch angle information is shown. This is supressed since this is the one spatial dimension by which the first operation mode is reduced. By suppressing this information focusing of the surgeon to achieving a proper pitch angle is facilitated, since the navigation device automatically monitors maintaining of proper yaw angle and indicates just any yaw deviations.

As a next step, the pitch angle is to be set. The surgeon then moves the handheld surgical tool into the desired pitch position, as verified by the fluoroscopic view generated by the C-arm 88 now moved in a position orthogonal to the previous one (see FIG. 5). Once it is ascertained that the pitch angle is proper, and still the desired heading angle is maintained, the surgeon will press the set key 35 again. The comparator 4 then switches into the second operating mode. In this mode the trajectory of the surgical tool is fully "locked-in". Any deviation of the instrument from that selected position, either in pitch or in yaw or both, will be detected by the comparator 4 in said second operating mode and will be shown by the feedback device 5. For example, a serious deviation to the right and a mild (but no longer tolerable) deviation upwards is indicated in FIG. 3d. The surgeon needs to adjust both, yaw and pitch, in order to regain the desired trajectory, and once he has accomplished this indication like that in FIG. 3c will be given.

In order to avoid an oversensitive action of the feedback device, a tolerance module 51 is provided. It is set to a tolerance criteria defining an individual level of tolerance for each angle. Examples for tolerance angle may be a maximum of two degrees.

Figure 5B:
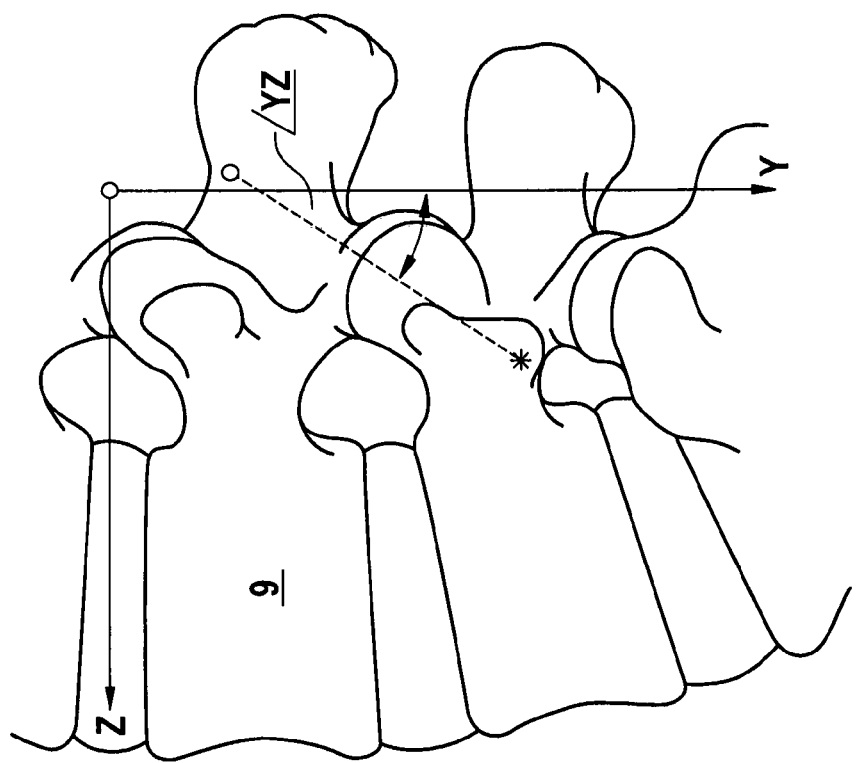
FIG. 5a, b: an overview similar to FIG. 4 but with the C-arm in a different orientation and the corresponding detail view of the spinal column.
Figure 5A:
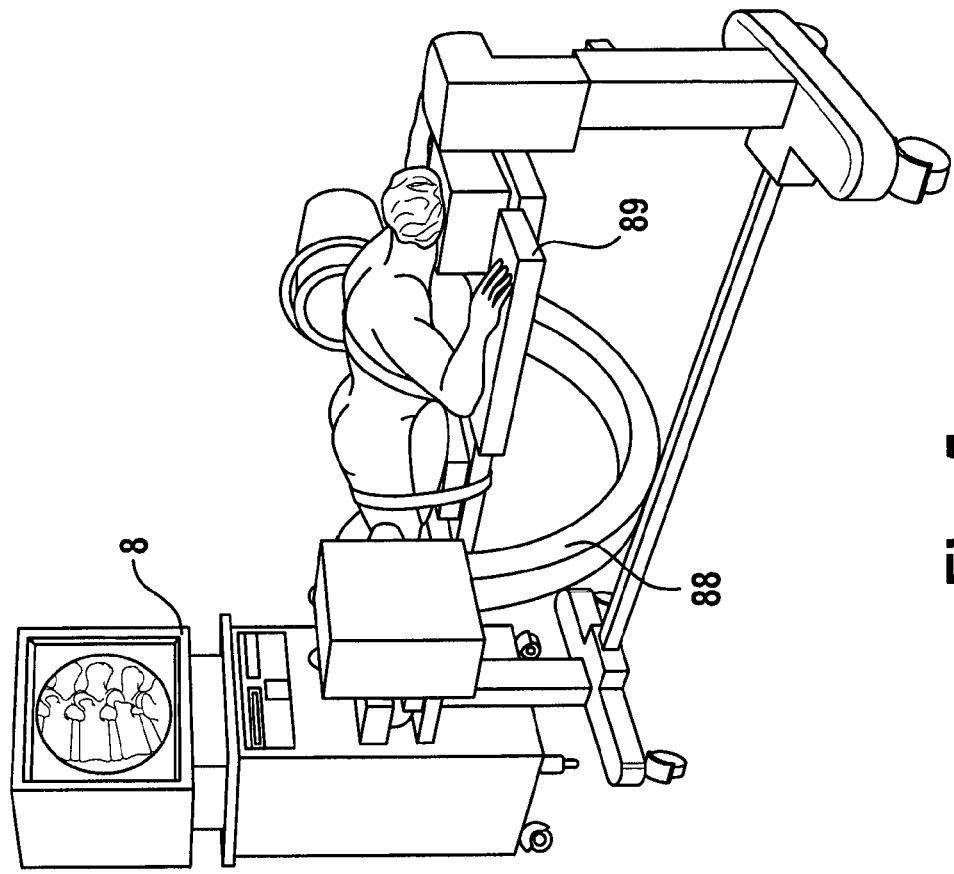
Figure 6B:
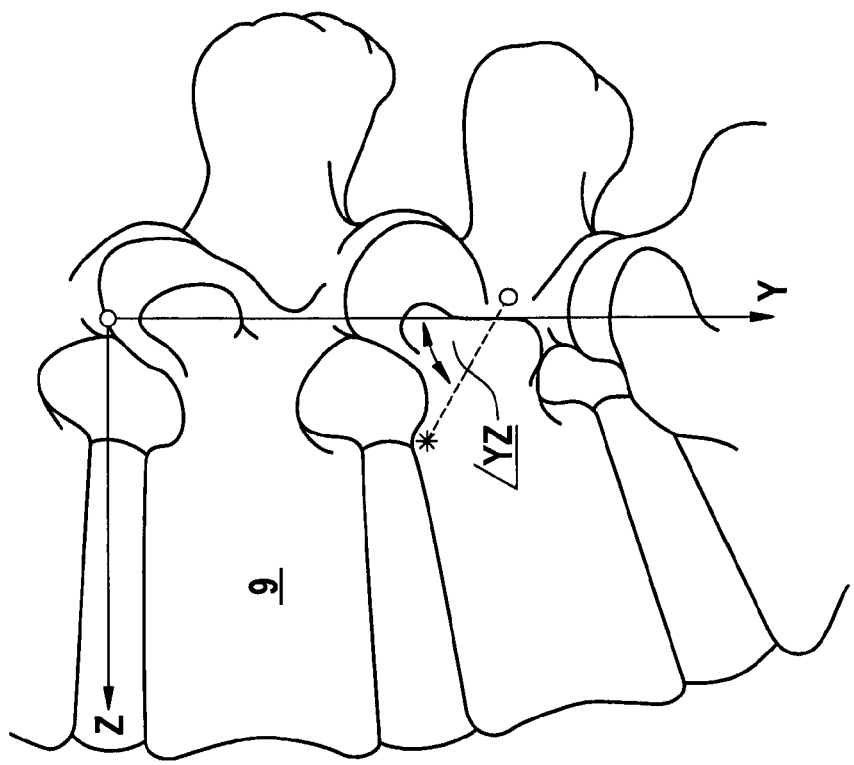
FIG. 6a, b: detailed views in two different orientations like in FIGS. 4 and 5 for a different application.
Figure 6A:
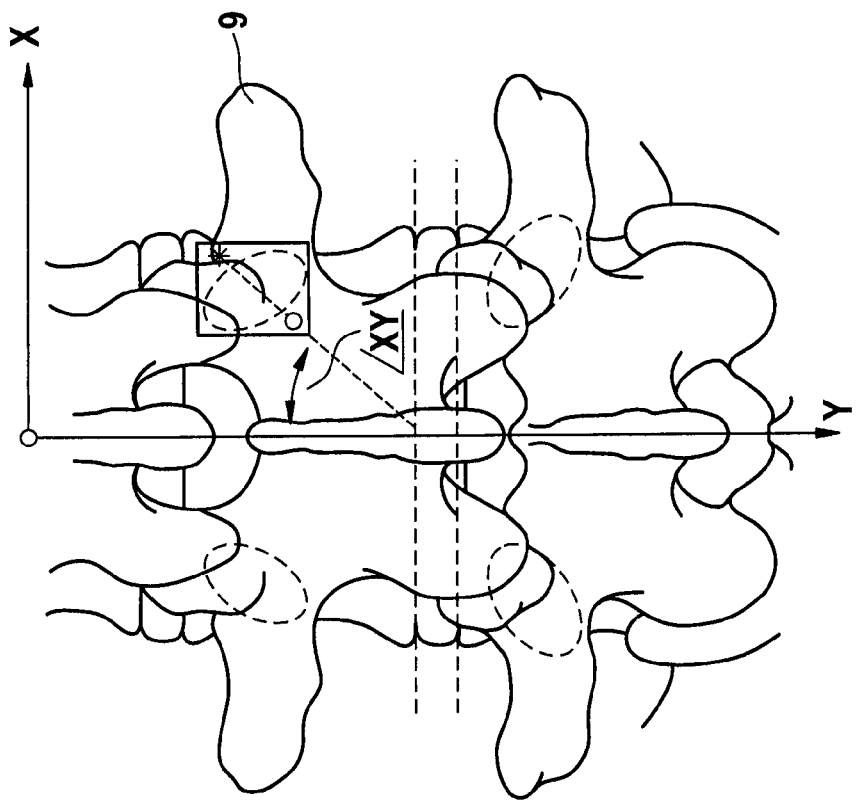

The invention has application for any screw trajectory, and another example would be for placement of pedicle screws. FIGS. 4b and 5b illustrate the radiographic landmarks which would be used for pedicle screws placed in a "cortical" trajectory. The starting point in the AP plane is defined as the empty space between the pedicle and an imaginary box drawn around the pedicle, shown as a small circle in FIG. 4b. The endpoint would be the superior-lateral aspect of the pedicle near the junction of the vertebral body, as shown by a star in FIG. 4b. These are well-known landmarks which can be used by the surgeon to choose a trajectory in the AP plane.

Further, in addition to the visual indication as provided by the display 54 (see FIG. 3a-d), aural and/or tactile indications can be given to the surgeon. For the tactile indication, vibration actuators in the left and right lateral side and in the upper and bottom section of the handle 1 will be activated as necessary in order to indicate a deviation to the left or right or to the top and to the down direction. A correct position will be achieved when all vibration actuators will be silenced. The strength of the activity of the vibration actuator may indicate a degree of deviation. Similarly, an aural indication can be given by the loudspeaker 53 (which may also be an earpiece). The control unit 53' is configured to vary pitch of a tone depending on a pitch deviation, like going to a higher tone if the pitch angle is too high and going to a lower tone if the pitch angle will be too low. Further, a continuous tone will be emitted if the heading is centered, the continuous tone becoming like a series of dashes if a deviation to the left will be detected and will become a series of dots if a deviation to the right will be detected, gradually blending over to a continuous tone as soon as the centered position will be regained. Thereby the surgeon can re-center the position and maintain the original trajectory without having even to look.

It is to be noted that the display 54 can preferably be on a different device as part of a two-piece construction. The different device may be a handheld or tablet computer. Thereby, an inexpensive and very efficient means is provided to give visual indication to the surgeon and his team.

The invention claimed is:
1. A handheld surgical tool comprising:
   a handle,
   an instrument shaft,
   a navigation device, the navigation device comprising:
      at least one sensor unit for sensing positional data,
      a computing unit configured to determine a position of the handheld surgical tool in space based on signals of the sensor unit,
      at least one set key, and
      a position memory configured to store a data set for a position of the handheld surgical tool upon activation of the at least one set key,
   a second computing unit operatively connected to the position memory, the second computing unit being configured to operate in at least two different operation modes and for generation of a deviation signal,
   wherein in a second operation mode the second computing unit compares the actual position of the handheld surgical unit to a position of the handheld surgical unit stored when the at least one set key is pressed,
   wherein in a first operation mode the second computing unit compares the actual position of the handheld surgical unit to a position of the handheld surgical unit stored when the at least one set key is pressed, the comparison in the first operation mode being a reduced comparison that does not compare at least one spatial dimension that the second operation mode does not lack, and a feedback device for receiving the deviation signal, the feedback device being configured to indicate direction of any deviation.

2. The handheld surgical tool of claim 1, wherein the feedback device is configured to suppress indication of the at least one spatial dimension in the first operation mode.

3. The handheld surgical tool of claim 1, wherein the feedback device is configured to indicate the deviation qualitatively.

4. The handheld surgical tool of claim 1, wherein the feedback device is configured to suppress indication of a deviation below a presetable threshold.

5. The handheld surgical tool of claim 1, wherein the feedback device is a two-part construction, having an indicator located remotely.

6. The handheld surgical tool of claim 5, wherein the indicator is located on a separate display.

7. The handheld surgical tool of claim 1, comprising a remote display for indicating the direction of the deviation.

8. The handheld surgical tool of claim 7, wherein the remote display is a hybrid display for showing imagery of a patient.

9. The handheld surgical tool of claim 1, comprising a reference base provided at an exterior surface of the surgical tool.

10. The handheld surgical tool of claim 9, comprising a key configured for zeroing the navigation device.

11. The handheld surgical tool of claim 1, comprising a third computing unit configured to determine a position of a tip of the instrument shaft and a position of another instrument attached to the instrument shaft.

12. The handheld surgical tool of claim 1, wherein the position memory is a duplex memory having a first memory unit and a second memory unit, wherein the second memory unit is configured for storing a full data set for the position forming a full position indication, and the first memory unit is configured for storing a subset only, wherein the subset lacks data for at least one degree of freedom in the position in space to form an incomplete position indication.

13. The handheld surgical tool of claim 1, comprising a rechargeable battery operatively connected to a wireless charging unit.

14. The handheld surgical tool of claim 1, wherein the set key comprises a momentary switch, a sensor switch, or a voice controlled switch.

15. The handheld surgical tool of claim 1, wherein the sensor unit comprises accelerometers, rate gyroscopes, or magnetometers.

16. The handheld surgical tool of claim 15, wherein the sensor unit comprises sensors in at least a 3-axis configuration.

17. The handheld surgical tool of claim 1, comprising an interface configured to supply positional data of the handheld surgical tool to an external system.

18. The handheld surgical tool of claim 1, wherein the feedback device is configured to indicate magnitude of any deviation.

19. The handheld surgical tool of claim 1, wherein the feedback device is configured to indicate the deviation non-numerically.

20. The handheld surgical tool of claim 1, wherein the feedback device is configured to indicate the deviation by at least one of a visual, an aural, and a tactile indication.

21. The handheld surgical tool of claim 1, comprising a third computing unit configured to determine a position of a tip of the instrument shaft or a position of another instrument attached to the instrument shaft.

22. A method for orienting a handheld surgical tool with autonomous navigation, the handheld surgical tool comprising a handle, an instrument shaft and a navigation device, the navigation device comprising at least one sensor unit for sensing positional data, a computing unit configured to determine a position in space based on signals of the sensor unit, at least one set key and a position memory configured to store a data set for position upon activation of the at least one set key, and a second computing unit operatively connected to the position memory, the method comprising:
positioning the handheld surgical tool at a first location and storing in the position memory a first subset of positional data corresponding to the first location, wherein the first subset of positional data lacks at least one first spatial dimension,
comparing an actual position of the handheld surgical tool against a position stored in the position memory using the subset of positional data in a first operation mode,
generating a first deviation signal based on a result of the comparison,
switching to a second operation mode by command,
comparing an actual position of the handheld surgical tool against a position stored in the position memory using positional data that does not lack the at least one first spatial dimension in the second operation mode,
providing a feedback about direction of any deviation to the user in the first operation mode and in the second operation mode.

23. The method of claim 22, comprising providing a feedback about magnitude of any deviation to the user in the first operation mode and in the second operation mode.

24. The method of claim 22, the method further comprising:
positioning the handheld surgical tool at a second location and storing in the position memory a second subset of positional data corresponding to the second location in the first operation mode, wherein the second subset of positional data lacks at least one second spatial dimension, the second spatial dimension being different from the first spatial dimension.

25. The method of claim 24, the method further comprising:
combining the first subset of positional data and the second subset of positional data to create a full positional data set,
wherein comparing the actual position of the handheld surgical tool against a position stored in the position memory using positional data in the second mode comprises comparing the actual position of the handheld surgical tool against the combined full positional data set.

* * * * *